United States Patent
Haller et al.

(10) Patent No.: US 8,166,803 B2
(45) Date of Patent: *May 1, 2012

(54) METHOD FOR THE QUANTITATIVE DETERMINATION OF AN AGING EFFECT ON MOTOR OIL

(75) Inventors: Volker Haller, Holzgerlingen (DE); Markus Niemann, Beckingen (DE); Thomas Hilberath, Eningen (DE); Gerald Hamm, Herrenberg (DE); Rolf Speicher, Tuebingen (DE); Monika Scherer, Reutlingen (DE); Udo Kaess, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 763 days.

This patent is subject to a terminal disclaimer.

(21) Appl. No.: 11/886,698

(22) PCT Filed: Jan. 25, 2006

(86) PCT No.: PCT/EP2006/050446
§ 371 (c)(1),
(2), (4) Date: Jan. 30, 2009

(87) PCT Pub. No.: WO2006/097381
PCT Pub. Date: Sep. 21, 2006

(65) Prior Publication Data
US 2009/0211342 A1    Aug. 27, 2009

(30) Foreign Application Priority Data
Mar. 18, 2005   (DE) .......................... 10 2005 012 454

(51) Int. Cl.
*G01N 33/28* (2006.01)

(52) U.S. Cl. ..................................... 73/53.05; 73/54.01
(58) Field of Classification Search .................... 379/68, 379/69, 70, 72, 74; 73/53.05
See application file for complete search history.

(56) References Cited

U.S. PATENT DOCUMENTS

| 4,007,629 A | * | 2/1977 | Hochstein | ..................... 73/53.05 |
| 5,750,887 A | * | 5/1998 | Schricker | ..................... 73/114.55 |
| 6,223,589 B1 | * | 5/2001 | Dickert et al. | ................ 73/61.45 |
| 7,275,418 B2 | * | 10/2007 | Niemann et al. | .............. 73/53.07 |
| 2004/0123644 A1 | * | 7/2004 | Jakoby et al. | ................. 73/19.11 |

(Continued)

FOREIGN PATENT DOCUMENTS

EP    0 866 428    9/1998

(Continued)

OTHER PUBLICATIONS

International Search Report, PCT International Patent Application No. PCT/EP2006/050446, dated Jun. 13, 2006.

(Continued)

*Primary Examiner* — Hezron E Williams
*Assistant Examiner* — Gregory J Redmann
(74) *Attorney, Agent, or Firm* — Kenyon & Kenyon LLP

(57) ABSTRACT

The quantitative determination of aging effects on motor oil is of great interest. According to a method, two variables of the motor oil are detected, one of the two variables being the viscosity and the other variable being the acid content of the motor oil. A first deviation of the detected first variable from a default value is then determined, and the second variable is estimated based on the deviation. By determining a second deviation of the estimated second variable from the detected second variable, the second deviation is determined as a measure of the aging effect on the motor oil. Since various aging effects influence the two variables in different manners, individual aging effects may be quantitatively determined in a targeted manner.

7 Claims, 1 Drawing Sheet

FOREIGN PATENT DOCUMENTS

| | | |
|---|---|---|
| JP | 2000-130240 | 5/2000 |
| JP | 2003-107000 | 4/2003 |

OTHER PUBLICATIONS

Wang, "Road Tests of Oil Condition Sensor and Sensing Technique," Sensors and Actuators B, vol. 73, No. 2-3, Mar. 10, 2001, pp. 106-111, XP004317265, ISSN: 0925-4005.

Wang, "Engine Oil Condition Sensor: Method for Establishing Correlation with Total Acid Number," Sensors and Actuators B, vol. 86, No. 2-3, Sep. 20, 2002, pp. 122-126, XP004380179, ISSN: 0925-4005.

\* cited by examiner

METHOD FOR THE QUANTITATIVE DETERMINATION OF AN AGING EFFECT ON MOTOR OIL

FIELD OF THE INVENTION

The present invention relates to a method for the quantitative determination of at least one aging effect on motor oil.

Although the present invention is described below with reference to the quantitative determination of the effects on oxidation or acidification of a motor oil, the present invention is not limited thereto, and relates in general to methods which determine the aging effects on motor oil.

BACKGROUND INFORMATION

Motor oils are used in internal combustion engines for lubrication of movable parts in order to reduce the friction and wear of metal surfaces which are moved with respect to one another. The motor oil is subjected to multiple aging processes necessitating that the oil be changed after a certain period. It is of great interest to provide a sensor device and a method which are able to detect the state of the oil in an internal combustion engine that is in operation.

The state of the motor oil is influenced in various ways by numerous aging processes. The effect of some aging processes on the characteristics and composition of the motor oil is known. In addition, these aging processes may be identified by certain processes in an engine or devices connected to the engine. Conversely, possible incorrect settings or defects in the engine or in the connected devices may be detected from the state of the oil.

Two aging effects are the waste heat from the engine and the inflow of atmospheric oxygen, which result in oxidation and acidification of the oil. The oxidation results in increased viscosity of the oil. Determination of the viscosity thus allows a determination of the degree of oxidation. Since carboxylic acids are produced by oxidation of the motor oil and the quantity of carboxylic acids is therefore a function of the degree of oxidation, the proportion of these acids in the oil may also be detected via the viscosity. However, this very simple test method does not take into account additional effects which contribute to an increase in the viscosity of the oil without changing the acid content, such as a clogged exhaust gas aftertreatment device, for example, which increases the soot content in the engine.

In addition, the quantity of blow-by gases is not detected, since these result only in an increase in the proportion of acid, which cannot be directly detected via the viscosity.

SUMMARY

The method according to example embodiments of the present invention for quantitative determination of an aging effect on motor oil includes: detection of two variables of the motor oil, one of the two physical variables being the viscosity and the other variable being the acid content of the motor oil; determination of a first deviation of the detected first variable from a first default value; estimation of the second variable based on the difference; and determination of a second deviation of the estimated second variable from the detected second variable as a measure of the aging effect on the motor oil.

One advantage of the present method is that the effects which act only on the acid content or which only alter the viscosity of the oil may be detected in a targeted manner.

When the estimated second variable is larger than the detected second variable, the aging effect may be identified as a first aging effect which influences the first variable, and in the converse second case, the aging effect may be identified as a second aging effect which influences the second variable.

An inflowing quantity of blow-by gases and/or a proportion of sulfur in the motor oil which influence the acid content may be determined as one of the aging effects, or an inflowing quantity of soot particles and/or a nitration process in the oil which influence the viscosity may be determined as the other aging effect.

The permittivity or the specific resistance of the motor oil may be detected as a third variable, and the soot content in the motor oil may be determined based on this variable.

A temperature of the motor oil may be determined, the default value may be selected as a function of the temperature, and the second variable may be estimated based on the temperature of the motor oil.

A service life of the motor oil may be plotted, and the default value may be selected as a function of the service life.

Exemplary embodiments of the present invention as well as advantageous refinements are illustrated with reference to the figures of the schematic drawings, and are explained in greater detail in the following description.

DETAILED DESCRIPTION

Figure 1:
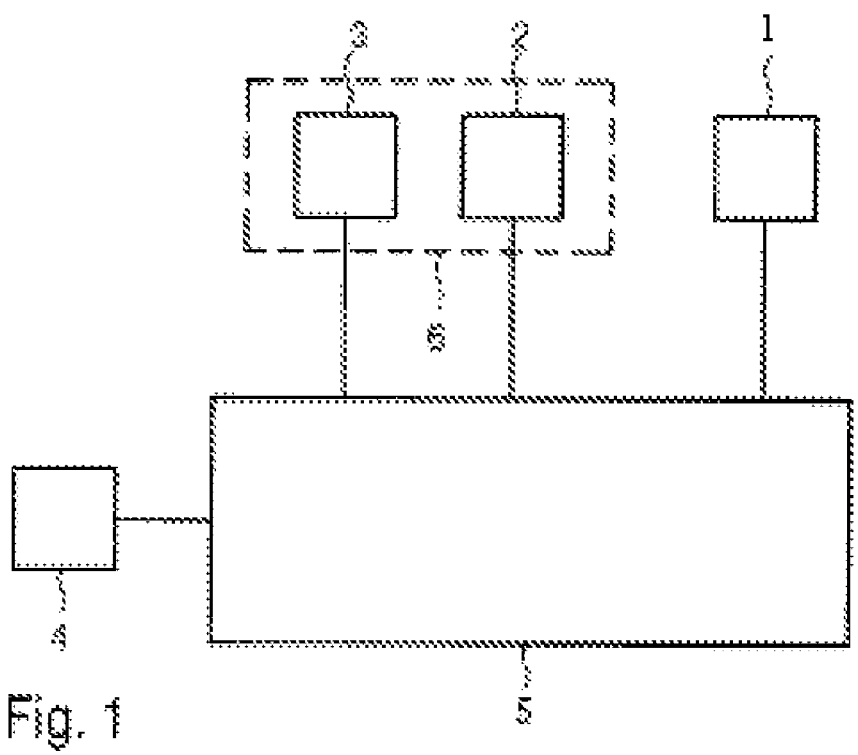
FIG. 1 shows a block diagram of an example embodiment of the present invention.

In the figures, similar or functionally similar features are denoted by the same reference numerals unless indicated otherwise.

Tests of motor oils are currently used to determine the state of an engine. Numerous characteristics of an engine have various types of effects on the state of an oil. The motor oil is typically oxidized by the inflow of atmospheric oxygen and by the waste heat from the engine. Aldehydes, ketones, and carboxylic acids, among other substances, are produced by the oxidation. These substances may further react in additional chemical reactions to produce sludge-like deposits which are mostly insoluble in oil, and may solidify on metal surfaces. Other products of aging in the oils are liquid and cause an increase in viscosity. Based on laboratory tests, the degree of oxidation of the motor oil and therefore its viscosity is known for typical loads on the engine as a function of the service life of the motor oil. If there are significant differences from the expected values, in particular a greatly increased viscosity, a conclusion may be drawn concerning a malfunction of the engine, the oil filter, exhaust gas aftertreatment devices, etc.

A further reason for monitoring the viscosity of the oil is that increased friction and wear on the elements occur when a critical viscosity value is exceeded. If the viscosity of the oil is less than a critical value, this may result in separation of the protective lubricating film between the parts, which in the worst case causes "seizure" of the engine. The motor oil must therefore be changed before these viscosity values are reached. Specifying a maximum elapsed mileage provides a large safety margin so that the viscosity remains below the critical value. However, it is disadvantageous that the oil is generally changed much earlier than necessary. As a result of continuous monitoring of the viscosity, the safety margin may be reduced and on average the oil may thus be used for a longer period.

A further criterion which makes an oil change absolutely necessary is an excessive acid content in the oil. The acids, for example the carboxylic acids, in the motor oil are buffered by the addition of basic additives. The acids intensify the corrosion, in particular of nonferrous metals. Furthermore, the acids in the oil have a catalytic effect on the oxidation of the oil. Thus, in a first approximation the acid content of the motor oil is proportional to the oxidation, and therefore is linearly dependent on the viscosity of the motor oil.

The viscosity is therefore used as an auxiliary variable for the evaluation of the acid content. However, blow-by gases and sulfur from the fuel also result in additional formation of acids, independent from the oxidation. Thus, from an analysis of the viscosity of the motor oil, it is not possible to draw a conclusion concerning the contribution of these blow-by gases and/or the supplied sulfur. However, detection of unusually high blow-by gases is of interest, since these indicate, for example, deposits on piston rings and suboptimal sealing of the crankcase. In addition, an increase in the acid content indicates that the basic additives in the motor oil are depleted. After the basic additives in the motor oil are depleted, the degree of oxidation of the motor oil and thus also the viscosity of the motor oil increase exponentially. Therefore, after this point in time it is extremely advisable to promptly change the oil.

FIG. 1 illustrates an example embodiment of the present invention. An acid sensor 1 and a viscosity sensor 2 are immersed in the motor oil to be tested. A permittivity sensor 3, which may be arranged as a combined viscosity/permittivity sensor, may also be immersed in the motor oil. The signals from the sensors are processed by a data processing device 5. A service life detection device 4 may be provided which determines how long the motor oil has been in use, the maximum temperatures the oil has experienced, the average heat to which the motor oil has been exposed, and the rotational speeds at which the engine has been operated, or additional detected engine parameters. All or part of these data may be provided to data processing device 5 for evaluation of the signals from the viscosity, permittivity, and acid sensors.

Figure 2:
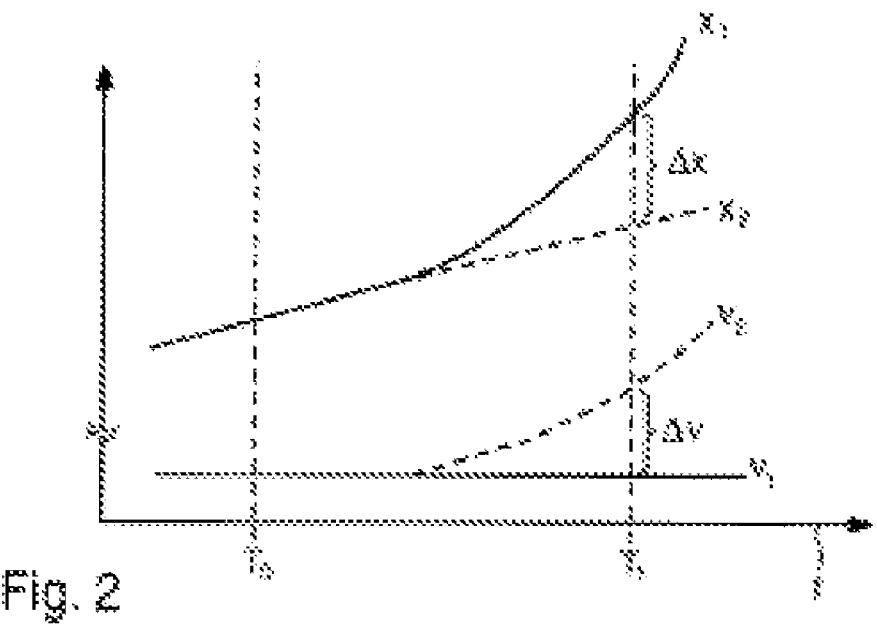
FIG. 2 shows a graphical illustration for explaining an example embodiment of the present invention.

FIG. 2 provides an illustration for explaining an evaluation method of data processing device 5. Viscosity v and acid content x of a motor oil are illustrated as a function of time t. The variables may be detected by corresponding sensor devices 1, 2, 3 at a point in time $T_0$, $T_1$. At a first point in time $T_0$, acid sensor 1 detects acid content $x_1$, and the viscosity sensor detects viscosity $v_1$. A model is provided in data processing device 5 which is able to estimate viscosity $v_1$ based on acid content $x_1$, with the assumption that only the oxidation of the motor oil results in formation of acids, in particular carboxylic acids. A comparison of estimated viscosity $v_2$ with detected viscosity $v_1$ results in no difference at point in time $T_0$; i.e., no additional influences act on the motor oil which result in an increase in the viscosity or the acid content in the motor oil.

At point in time $T_1$, as an example the response of the motor oil is illustrated when the acid content, for example as a result of blow-by gases, is greatly increased. In a first step a difference $\Delta x$ or a deviation of detected acid content $x_1$ from a default value $x_2$ or expected acid content $x_2$ is determined. The default value may be the acid content of a new motor oil, or may take into account a degree of oxidation and the associated proportion of acid in a motor oil, which is determined by the data processing device based on the service life, the maximum temperatures, the average temperature, and the rotational speeds of the engine. A viscosity $v_2$ is determined based on deviation $\Delta x$. This may be performed in a simple manner by the fact that a proportional dependency of the viscosity on the acid content is assumed, and, corresponding to the default value of the acid content, a default value is also provided for the viscosity. Viscosity $v_2$ estimated in this manner is then compared to detected viscosity $v_1$. If a deviation $\Delta v$ results, this is attributed to additional influences (not strictly oxidation due to heat and air inflow and formation of carboxylic acids). If estimated viscosity $v_2$ is greater than detected viscosity $v_1$, as illustrated in FIG. 2, the reason is that an influence has increased the viscosity without simultaneously increasing the acid content. One such influence is soot particles, which pass into the motor oil in increased quantities as a result of, among other elements, exhaust gas aftertreatment devices in these engines. An unusually large difference $\Delta v$ in detected viscosity $v_1$ compared to estimated viscosity $v_2$ would be cause for cleaning the exhaust gas aftertreatment device. The second converse case, i.e., when estimated viscosity $v_2$ is less than detected viscosity $v_1$, results from the formation of acids which are not produced by oxidation of motor oil. These additional acids are produced from sulfur, among other substances, which enters the motor oil via the fuel and also via blow-by gases. An unusually high value of deviation $\Delta v$ indicates, among other things, deposits on piston rings.

The permittivity and/or the specific electrical conductance of the motor oil may be determined as additional variables. By use of these variables a conclusion may be drawn in particular concerning the proportion of soot in the motor oil.

List Of Reference Characters
1 Acid sensor
2 Viscosity sensor
3 Permittivity sensor
4 Detection device
5 Data processing device
t Time
v Viscosity
x Acid content
$T_0$, $T_1$ Points in time
$x_1$ Detected acid content
$v_1$ Detected viscosity
$v_2$ Estimated viscosity
$x_2$ Default value
$\Delta x$ Deviation
$\Delta v$ Deviation

What is claimed is:
1. A method for quantitatively determining at least one aging effect on motor oil, comprising:
   detecting two physical variables of the motor oil, one variable being viscosity and the other variable being acid content of the motor oil;
   determining a first deviation of a first one of the variables from a first default value;
   estimating a second one of the variables based on the deviation; and
   determining a second deviation of the estimated second one of the variables from the detected second one of the variables as a measure of the aging effect on the motor oil.

2. The method according to claim 1, wherein when the estimated second one of the variables is larger than the detected second one of the variables, the aging effect is identified as a first aging effect which influences the first one of the variables, and when the detected second one of the variables is larger than the estimated second one of the variables the aging effect is identified as a second aging effect which influences the second one of the variables.

3. The method according to claim 1, wherein at least one of (A) at least one of (a) an inflowing quantity of blow-by gases and (b) a proportion of sulfur in the motor oil which influence the acid content are determined as one of the aging effects and (B) at least one of (a) an inflowing quantity of soot particles and (b) a nitration process in the oil which influence the viscosity are determined as another aging effect.

4. The method according to claim 1, wherein at least one of (a) permittivity and (b) a specific resistance of the motor oil is detected as a third variable, and a soot content in the motor oil is determined based on the variable third variable.

5. The method according to claim 1, wherein a temperature of the motor oil is determined, the first default value is selected as a function of the temperature, and the second one of the variables is estimated based on the temperature of the motor oil.

6. The method according to claim 1, wherein a service life of the motor oil is plotted, and the first default value is selected as a function of the service life.

7. A method for quantitatively determining at least one aging effect on motor oil, the at least one aging effect being at least one of a blow-by gas that has flown towards the motor oil, sulfur or soot particles in the motor oil, or a nitration process of the motor oil, comprising:

detecting two physical variables of the motor oil, one variable being viscosity and the other variable being acid content of the motor oil;

determining a first deviation of a first one of the variables from a first default value;

estimating a second one of the variables based on the deviation; and determining a second deviation of the estimated second one of the variables from the detected second one of the variables as a measure of the aging effect on the motor oil, wherein when the detected second variable is more than the estimated second variable, blow-by gas flown towards the motor oil or sulfur in the motor oil has contributed to the aging of the motor oil, and wherein when the detected second variable is less than the estimated second variable, soot particles in the motor oil or the nitration process of the motor oil has contributed to the aging of the motor oil.

\* \* \* \* \*